United States Patent
Tsao et al.

(10) Patent No.: US 9,938,328 B2
(45) Date of Patent: Apr. 10, 2018

(54) USE OF PEDF-DERIVED POLYPEPTIDES FOR TREATING ALOPECIA AND/OR HAIR DEPIGMENTATION

(71) Applicant: MacKay Memorial Hospital, Taipei (TW)

(72) Inventors: Yeou-Ping Tsao, Taipei (TW); Tsung-Chuan Ho, Taipei (TW)

(73) Assignee: MacKay Memorial Hospital, Taipei City (TW)

( * ) Notice: Subject to any disclaimer, the term of this patent is extended or adjusted under 35 U.S.C. 154(b) by 0 days.

(21) Appl. No.: 14/428,843

(22) PCT Filed: Sep. 17, 2012

(86) PCT No.: PCT/CN2012/081508
§ 371 (c)(1),
(2) Date: Mar. 17, 2015

(87) PCT Pub. No.: WO2014/040302
PCT Pub. Date: Mar. 20, 2014

(65) Prior Publication Data
US 2015/0239946 A1 Aug. 27, 2015

(51) Int. Cl.
*A61K 38/00* (2006.01)
*C07K 14/47* (2006.01)
*C07K 14/81* (2006.01)

(52) U.S. Cl.
CPC ............ *C07K 14/47* (2013.01); *C07K 14/811* (2013.01); *A61K 38/00* (2013.01)

(58) Field of Classification Search
None
See application file for complete search history.

(56) References Cited

U.S. PATENT DOCUMENTS

2008/0293626 A1 11/2008 Tong et al.
2009/0069241 A1 3/2009 Barnstable et al.

FOREIGN PATENT DOCUMENTS

| CN | 101014358 A | 8/2007 |
|---|---|---|
| CN | 101506226 A | 8/2009 |
| EP | 2508196 A1 | 10/2012 |
| JP | 2007-509984 A | 4/2007 |
| JP | 2007-197330 A | 8/2007 |
| WO | 2005/041887 A2 | 5/2005 |
| WO | 2014/023007 A1 | 2/2014 |
| WO | 2014/043861 A1 | 3/2014 |
| WO | 2014/043871 A1 | 3/2014 |

OTHER PUBLICATIONS

First Office Action dated May 31, 2016, by the Japan Patent Office in related Japanese Patent Application No. JP 2015-531418, with Google English machine translation (11 pages).

Liu, Hua, et al., "Identification of the antivasopermeabifity effect of pigment epithelium-derived factor and its active site", PNAS, Fol. 101, No. 17, Apr. 27, 2004; pp. 6605-6610.
Bilak, Masako, et al., "Identification of the Neuroprotective Molecular Region of Pigment Epithelium-Derived Factor and Its Binding Sites on Motor Neurons"; The Journal of Neuroscience, vol. 22, No. 21, Nov. 1, 2002; pp. 9378-9386.
Alberdi, Elena, et al., "Binding of Pigment Epithelium-derived Factor (PEDF) to Retinoblastoma Cells and Cerebellar Granule Neurons: Evidence for a PEDF Receptor"; The Journal of Biological Chemistry, vol. 274, No. 41, Oct. 29, 1999 issue; pp. 31605-31612.
International Search Report issued in PCT/CN2012/081508 dated Jun. 27, 2013 (4 pages).
Supplementary European Search Report dated Feb. 2, 2016, issued by the European Patent Office in related European Patent Application No. EP-12884514 (4 pages).
Sawaya, Marty E., "Novel Agents for the Treatment of Alopecia"; Seminars in Cutaneous Medicine and Surgery, vol. 17, No. 4 (Dec. 1998); XP005470225, ISSN: 1085-5629, DOI: 10.1016/S1085-5629(98)80024-2; pp. 276-283.
Patent Examination Report No. 1 (Office Action) dated Jun. 30, 2016, issued by the Australian Patent Office in related Australian Patent Application No. 2012389654 (7 pages).
EP Communication pursuant to Article 94(3) EPC (Office Action) dated Oct. 19, 2016, issued by the European Patent Office in related European Patent Application No. 12884514.6 (4 pages).
Steele et al., "Pigment epithelium-derived factor: neurotrophic activity and identification as a member of the serine protease inhibitor gene family", Proc Natl Acad Sci USA, vol. 90, pp. 1526-1530, Dated Feb. 15, 1993 (5 pages).
Office Action issued in Chinese Application No. 201280077072.5, dated Feb. 28, 2017 (15 pages).
Notice of Grounds for Preliminary Rejection (Office Action) dated Jan. 16, 2017, issued by the Korean Intellectual property Office (KIPO) in related Korean Patent Application No. KR 10-2015-7009719, with English translation (9 pages).
Final Office Action dated Apr. 11, 2017, issued by the Japan Patent Office in corresponding Japanese Patent Application No. JP 2015-531418, with USPTO Global Dossier English translation (6 pages).
EPO Communication pursuant to Article 94(3) EPC ("Office Action") dated Jul. 11, 2017, by the European Patent Office in corresponding European Patent Application No. EP-12884514.6 (3 pages).

*Primary Examiner* — Thomas S Heard
(74) *Attorney, Agent, or Firm* — Osha Liang LLP (57) ABSTRACT

A method for treating alopecia and/or hair depigmentation includes administering to a subject in need of such treatments a synthetic peptide, which has an amino acid sequence that has 20-44 amino acid residues and includes at least 20 consecutive residues that has at least 90% amino acid sequence identity to residues 16-35 of SEQ ID NO: 10. Also disclosed herein are pharmaceutical compositions containing the synthetic peptide; and uses thereof. According to various embodiments of the present disclosure, the synthetic peptide is useful in treating alopecia and/or hair depigmentation in a subject.

21 Claims, 4 Drawing Sheets

USE OF PEDF-DERIVED POLYPEPTIDES FOR TREATING ALOPECIA AND/OR HAIR DEPIGMENTATION

CROSS REFERENCE TO RELATED APPLICATIONS

This is a national phase application based on PCT/CN2012/081508, filed on Sep. 17, 2012, the disclosure of which is incorporated by reference in its entirety.

BACKGROUND OF THE INVENTION

1. Field of the Invention

The present disclosure relates to the treatment of alopecia and/or hair depigmentation. In particular, the disclosed invention relates to the use of PEDF-derived polypeptides for treating alopecia and/or hair depigmentation.

2. Description of Related Art

Alopecia means loss of hair from the head or body, and can be categorized as either cicatricial (scarring) alopecia or non-cicatricial (non-scarring) alopecia. In patients with cicatricial alopecia, the hair follicles would be destroyed and replaced with scar tissues, whereas in patients with non-cicatricial alopecia, there are no such irreversible damages. While not life-threatening, alopecia affects personal appearance, and therefore personal social interactions, self-esteem, and psychological wellbeing.

Non-cicatricial alopecia includes anagen effluvium, telogen effluvium, androgenic alopecia, and alopecia areata, each of which is resulted from a distinct biological defect. Depending on the type of alopecia a subject might be experiencing, its effects on the hair follicles differs accordingly.

Anagen effluvium is generally caused by abrupt cessation of mitotic activity in hair matrix cells of anagen hair follicles. As such, the hair follicles produce either no hair, or narrow defective hair sheaths which are predisposed to fracture and loss. Anagen Effluvium is common in patients underwent chemotherapy or radiotherapy. Generally, hair follicles would resume their original growth cycle once the cause of anagen effluvium ceases to exist. Hence, in most cases, re-growth of hair starts after the treatment ends. However, the color and texture of the newly grown hairs may be different from those of the original hairs.

Telogen effluvium occurs when cycling hair follicles enter the telogen phase of the hair growth cycle prematurely, thereby causing excessive shedding of hair. It may be caused by various stress-related conditions, including imbalanced diet, medications (e.g., beta blockers, calcium channel blockers, antidepressants, and non-steroidal anti-inflammatories, etc.), childbirth, high fevers, major surgery, an over- or under-active thyroid gland, severe infections, severe chronic illness, and severe psychological stress. Generally, hair loss appears 3 to 4 months after the individual had experienced any of the stress incidents; and the lost hair will be replaced within 6 to 12 months.

Androgenic alopecia (also known as male pattern baldness) is the most common type of male hair loss. Androgenic alopecia affects both male and female, although female subjects tend to lose less hair than male subjects. The underlying mechanism for androgenic alopecia is not well understood. However, it is believed that the hypersensitivity of hair follicles against dihydrotestosterone (a derivative of androgen) is associated with the development of androgenic alopecia in men. The hypersensitivity may cause the miniaturization of hair follicles and shorten the anagen period of hair follicle cells, thereby resulting in the formation of the club hair which is eventually shed from the hair follicle.

Currently, there are two drugs proved by the U.S. Food & Drug Administration (FDA) for the treatment of androgenic alopecia: topical minoxidil (brand name: ROGAINE®) and oral finasteride (brand name: Propecia®). Minoxidil is a potassium channel agonist that affects the hair follicles by extending the anagen period of hair follicles, stimulating the telogen-to-anagen transformation, and promoting the follicle size enlargement. Minoxidil is also applicable in the treatment of alopecia areata as well as anagen effluvium caused by chemotherapy. Finasteride is a competitive inhibitor of type II 5-α-reductase, an enzyme that converts testosterone to dihydrotestosterone (DHT). Therefore, finasteride treats androgenic alopecia by blocking the activity of type II 5-α-reductase. Although these two drugs stimulate hair regrowth in some patients, they are only effective during the medication period, and hence, the patients are advised to take the medication continuously. In addition, use of minoxidil or finasteride is occasionally found to be accompanied by a number of side effects. Possible side effects of minoxidil include scalp itching or rash; decreased libido; elevated heart rate; difficulty breathing; weight gain; and hypertrichosis. Possible side effects of finasteride include skin rash; breast enlargement or tenderness; testicular pain; decreased libido; decreased volume of ejaculate; and impotence.

Hair color is the result of pigmentation of the hair. When the supply of the pigment (i.e., melanin) from the melanocytes decreases, the newly grown hair would loss its original color and exhibits a lighter or even white color, a phenomenon generally known as hair depigmentation. Factors that cause hair depigmentation includes at least, aging, stress, disorders (e.g., piebaldism), etc. In addition, hair depigmentation is often found in newly grown hairs of patients whom previously underwent chemotherapy or radiotherapy. To date, there is no medical treatment that is effective in inducing the depigmented hair to regain its former color. Therefore, most people experiencing hair depigmentation have to cope with their appearances or to cover the depigmented hair by dying the hairs or by wearing a wig.

In view of the foregoing, there exists a need in the art for means that effectively treats various types of alopecia and/or hair depigmentation.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based, at least, on the finding that synthetic peptides derived from pigment epithelium-derived factor (PEDF) may protect hair follicles, and hence they are effective in preventing and/or ameliorating hair loss and/or hair depigmentation in a subject. Specifically, working examples provided herein indicate that various PEDF-derived synthetic peptides are capable of inhibiting hair follicle dystrophy and follicle cell apoptosis, and/or preventing immature differentiation of melanocyte stem cells (MSCs) in the hair follicles. The PEDF-derived synthetic peptides of this invention are, therefore, useful as an agent or a medicament for preventing and/or ameliorating hair loss and/or hair depigmentation.

Accordingly, in one aspect, the present disclosure is directed to a synthetic peptide for treating alopecia and/or hair depigmentation in a subject.

According to embodiments of the present disclosure, the synthetic peptide is 20-44 amino acid residues in length, and has an amino acid sequence that is at least 80% identical to SEQ ID NO: 10. Also, the amino acid sequence comprises at least 20 consecutive residues, which is at least 90% identical to residues 16-35 of SEQ ID NO: 10, such that the synthetic peptide is useful in treating alopecia and/or hair depigmentation.

According to optional embodiments of the present disclosure, at least 4 consecutive residues of the synthetic peptide are identical to residues 16-19 of SEQ ID NO: 10 (i.e., the "SLGA residues"). Non-limiting examples of such synthetic peptides include those respectively having an amino acid sequence of SEQ ID NO: 10 (44-mer), SEQ ID NO: 1 (39-mer), SEQ ID NO: 2 (34-mer), SEQ ID NO: 3 (29-mer), SEQ ID NO: 5 (24-mer), SEQ ID NO: 6 (20-mer), SEQ ID NO: 8 (MO 29-mer), and SEQ ID NO: 9 (MO 20-mer). In some embodiments of the present disclosure, the amino acid sequence of the synthetic peptide is SEQ ID NO: 10 (44-mer), SEQ ID NO: 3 (29-mer), SEQ ID NO: 5 (24-mer), or SEQ ID NO: 6 (20-mer).

According to various embodiments of the present disclosure, the alopecia may be anagen effluvium (e.g., those caused by the chemotherapy or radiotherapy), telogen effluvium (e.g., those caused by the stress, diet imbalance, medications, or infections), or androgenic alopecia.

In some embodiments, the hair depigmentation may be caused by the chemotherapy or radiotherapy. In some other embodiments, the hair depigmentation may be caused by stress or aging.

According to various embodiments of the present disclosure, the subject may be any animal classified as a mammal, including human.

In another aspect, the present disclosure is directed to a topical pharmaceutical composition for treating alopecia and/or hair depigmentation in a subject. The subject may be any animal classified as a mammal, including human.

According to one embodiment of the present disclosure, the topical pharmaceutical composition comprises a synthetic peptide according to any of the above-mentioned aspect/embodiments, and the synthetic peptide is present in an effective amount sufficient to treat alopecia and/or hair depigmentation in the subject. The pharmaceutical composition also comprises a pharmaceutically acceptable excipient for the synthetic peptide.

In various embodiments of the present disclosure, the topical pharmaceutical composition may be formulated into a solution, spray, aerosol, foam, cream, lotion, ointment, gel, or patch.

According to optional embodiments of the present disclosure, the synthetic peptide is present in the pharmaceutical composition in an amount of about 0.1-100 μM, and preferably, about 1-25 μM.

In yet another aspect, the present invention is directed to a method for treating alopecia and/or hair depigmentation in a subject. The subject may be any animal classified as a mammal, including human.

In one embodiment, the method comprises administering to the subject an effective amount of the synthetic peptide according to any of the above-mentioned aspect/embodiments. According to various embodiment of the present disclosure, the synthetic peptide may be delivered topically or systemically. Preferably, the synthetic peptide is administered topically.

According to optional embodiments, the synthetic peptide is formulated into a topical pharmaceutical composition according to the above-mentioned aspect/embodiments of the present disclosure. In one example, the present topical pharmaceutical composition may be applied onto the scalp of the subject.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

The present description will be better understood from the following detailed description read in light of the accompanying drawings.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the entire application (including the specification, examples, and appended claims) are collected here. Unless otherwise defined herein, scientific and technical terminologies employed in the present disclosure shall have the meanings that are commonly understood and used by one of ordinary skill in the related art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "peptide" denotes a polymer of amino acid residues. By the term "synthetic peptide" as used herein, it is meant a peptide which does not comprise an entire naturally occurring protein molecule. The peptide is "synthetic" in that it may be produced by human intervention using such techniques as chemical synthesis, recombinant genetic techniques, or fragmentation of the whole protein or the like. Throughout the present disclosure, the positions of any specified amino acid residues within a peptide are numbered starting from the N terminus of the peptide.

The term "stem cell" as used herein, refers to a cell that retains the capacity, under certain circumstances, to proliferate without substantially differentiating; as well as the capacity or potential, under particular circumstances, to differentiate to a more specialized or differentiated phenotype.

As used herein, "proliferating" and "proliferation" refers to an increase in the number of cells in a population by means of cell division.

"Percentage (%) amino acid sequence identity" with respect to the synthetic polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The terms "treatment" and "treating" are used herein to include preventative (e.g., prophylactic), curative, or palliative treatment that results in a desired pharmaceutical and/or physiological effect. Preferably, the effect is therapeutic in terms of partially or completely curing or preventing the alopecia or hair-depigmentation. Also, the term "treating" as used herein refers to application or administration of the synthetic peptide or pharmaceutical composition of the present disclosure to a subject, who has a medical condition, a symptom of the condition, a disease or disorder secondary to the condition, or a predisposition toward the condition, with the purpose to partially or completely alleviate, ameliorate, relieve, delay onset of, inhibit progression of reduce severity of, and/or reduce incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. As used herein, the symptom, disease, disorder or condition may be alopecia or hair-depigmentation. Treatment is generally "effective" if one or more symptoms or clinical markers are reduced as that term is defined herein.

The term "effective amount" as used herein refers to the quantity of a component which is sufficient to yield a desired response. The term "therapeutically effective amount" as used herein refers to the amount of the therapeutic agent in the pharmaceutical composition which results in a desired "effective treatment" as defined hereinabove. The specific therapeutically effective amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed. A therapeutically effective amount is also one in which any toxic or detrimental effects of the compound or composition are outweighed by the therapeutically beneficial effects.

The terms "application" or "administration" are used interchangeably herein to refer means providing a synthetic peptide or a pharmaceutical composition of the present invention to a subject to treat alopecia and/or hair-depigmentation. According to various embodiments of the present disclosure, topical application is a preferred route of administration. For example, the synthetic peptide or pharmaceutical composition of the present invention is topically applied to the biological surface (e.g., skin, scalp, or hair) of the subject such that the synthetic peptide or the present pharmaceutical composition reaches the target site (e.g., hair follicles) so as to prevent or ameliorate alopecia and/or hair depigmentation.

The term "excipient" as used herein means any inert substance (such as a powder or liquid) that forms a vehicle/carrier for the synthetic PEDF peptide(s) of the present disclosure. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

As used herein, a "pharmaceutically acceptable" component is one that is suitable for use with humans and/or animals without undue adverse side effects (such as toxicity, irritation, and allergic response) commensurate with a reasonable benefit/risk ratio. Also, each excipient must be "acceptable" in the sense of being compatible with the other ingredients of the pharmaceutical formulation.

The term "subject" refers to a mammal including the human species that is treatable with the synthetic peptides, compositions, and/or methods of the present invention. The term "subject" is intended to refer to both the male and female gender unless one gender is specifically indicated.

There are three stages of animal hair growth: catagen, telogen, and anagen. Anagen is the active growth phase of the hair during which the cells in the hair bulb are dividing rapidly and differentiating into hair shaft. On average, human scalp hairs stay in this active phase of growth for about 3-5 years, while murine hairs stay in anagen phase for about 11 days. The anagen phase is followed by a catagen phase. During this time, hair growth stops and about 70% of the follicles cells undergo apoptosis and re-absorption, thereby resulting in the formation of club hairs. The catagen phase is a transitional stage that lasts for about 1-2 weeks for human scalp hairs. After catagen, the hair goes into a telogen phase. Telogen is the resting phase, which lasts for about 3 months for human scalp hairs. During this phase, the hair follicle is completely at rest and the club hair is completely formed. As compared with anagen hairs, telogen hairs (club hairs) can be pulled out relatively easily and tend to shed.

Follicle stem cells (FSCs) and melanocyte stem cells (MSCs) reside in the bulge region of the hair follicle, and are responsible for hair regeneration and hair pigmentation, respectively. Many factors are known to jeopardize the stemness of the follicle stem cells and/or melanocyte stem cells. For example, these stem cells may lose their stemness under the action of aging, environmental oxidants, disorders associated with hair follicles, chemotherapy, or the subject's genetic makeup. Losing stemness may affect the life cycles of their progenies which in turn causes alopecia or hair depigmentation.

Pigment epithelium-derived factor (PEDF) is a multifunctional secreted protein that has anti-angiogenic, anti-tumorigenic, and neurotrophic functions. Human PEDF protein (SEQ ID NO: 11) is a secreted protein of roughly 50 kDa size and 418 amino acids in length. A 34-mer fragment (residues 44-77) and a 44-mer fragment (residues 78-121; SEQ ID NO: 10) of PEDF have been identified to have anti-angiogenic and neurotrophic properties, respectively.

The present disclosure is based, at least, on the finding that synthetic peptides derived from the 44-mer PEDF may protect hair follicles via a variety of mechanisms. For example, the synthetic peptide may inhibit the miniaturization of hair follicles, prevent the immature differentiation of melanocyte stem cells into melanocytes, and reduce the melanin clumping. Without being bound by any theory, it is believed that these protective mechanisms are helpful in maintaining the stemness of stem cells in hair follicles and/or retaining the progeny cells of such stem cells in their normal life cycle so that the hair follicles would produce healthy, normal hairs that are less prone to shed abnormally and/or preserve their original color. Another inventive feature of the present invention lies in that the synthetic peptides are much shorter (20-44 amino acid residues) than the full-length PEDF and thus overcomes the limitations associated with the clinical use of conventional protein drugs, including high manufacturing cost, low bioavailability, and poor pharmacokinetics. Accordingly, the present synthetic peptides are useful for treating alopecia and/or hair depigmentation.

Thus, in one aspect, the present disclosure is directed to a synthetic peptide for treating alopecia and/or hair depigmentation in a subject.

According to embodiments of the present disclosure, the synthetic peptide has 20-44 amino acid residues in length, and has at least 80% amino acid sequence identity with the amino acid sequence of VLLSPLSVATALSALSLGAEQRTESIIHRALYYDLISSPDIHGT (SEQ ID NO: 10). For example, the synthetic peptide may have an amino acid sequence identity of about 80, 81, 82, 83, 84, 85, 86, 87, 88, 89, 90, 91, 92, 93, 94, 95, 96, 97, 98, 99, or 100 percent with SEQ ID NO: 10. Also, the synthetic peptide comprises at least 20 consecutive residues that are at least 90% identical to residues 16-35 of SEQ ID NO: 10. Specifically, the 20 consecutive amino acid residues may have about 90, 91, 92, 93, 94, 95, 96, 97, 98, 99, or 100 percent amino acid sequence identity with residues 16-35 of SEQ ID NO: 10.

In one embodiment, the synthetic peptide is the 44-mer. Prior experiments conducted by the present inventors, such as those disclosed in the co-pending applications U.S. Ser. No. 13/428,996 and TW 100138168 (the entirety of which is incorporated herein by reference) and experiments provided hereinbelow, reveal that several short, synthetic PEDF peptides derived from the 44-mer, are capable of treating alopecia and/or hair depigmentation in a subject. Specifically, the Taiwan patent application No: 100138168 discloses that PEDF 44-mer is effective in preventing and/or ameliorating alopecia and hair depigmentation induced by chemotherapy or stress, as well as preventing and/or ameliorating androgenic alopecia.

For example, based on experiments disclosed in both the prior application and the present application, a 39-mer synthetic peptide having the sequence of LSVATALSALSLGAEQRTESIIHRALYYDLISSPDIHGT (SEQ ID NO: 1) is effective in treating alopecia and/or hair depigmentation in a subject. This 39-mer peptide corresponds to residues 83-121 of human PEDF and hence is a short variant derived from the known PEDF 44-mer (corresponding to residues 78-121 of PEDF). According to the process for estimating percentage of sequence identity between any two given sequences provided above, the 39-mer has a 100% amino acid sequence identity to the 44-mer, and the $11^{th}$-$30^{th}$ amino acid residues of the 39-mer has a 100% amino acid sequence identity to the amino acid residues 16-35 of the 44-mer.

In another example, a 34-mer synthetic peptide having the sequence of ALSALSLGAEQRTESIIHRALYYDLISSPDIHGT (SEQ ID NO: 2) is effective in treating alopecia and/or hair depigmentation in a subject, based on experiments disclosed in both the prior application and the present application. This 34-mer peptide corresponds to residues 88-121 of human PEDF. The 34-mer has a 100% amino acid sequence identity to the 44-mer, and the $6^{th}$-$25^{th}$ amino acid residues of the 34-mer has a 100% amino acid sequence identity to the amino acid residues 16-35 of the 44-mer.

Additionally, according to various examples hereinbelow, a 29-mer synthetic peptide having the sequence of SLGAEQRTESIIHRALYYDLISSPDIHGT (SEQ ID NO: 3) has been confirmed to be effective in preventing and/or ameliorating androgenic alopecia in a subject. The 29-mer is also believed to be effective in treating alopecia and/or hair depigmentation caused by chemotherapy or stress, based on experiments disclosed in both the prior application and the present application. This 29-mer peptide corresponds to residues 93-121 of human PEDF with a 100% amino acid sequence identity to the 44-mer. Also, the $1^{st}$-$20^{th}$ amino acid residues of the 29-mer has a 100% amino acid sequence identity to the amino acid residues 16-35 of the 44-mer.

In some examples, a 24-mer has been confirmed to be effective in preventing and/or ameliorating androgenic alopecia in a subject. Also, it is believed that the 24-mer is effective in treating alopecia and/or hair depigmentation caused by chemotherapy or stress, based on experiments disclosed in both the prior application and the present application. The 24-mer has the sequence of SLGAEQRTESIIHRALYYDLISSP (SEQ ID NO: 5), which corresponds to residues 93-116 of human PEDF. This 24-mer peptide has a 100% amino acid sequence identity to the 44-mer in which the first twenty amino acid residues thereof has a 100% amino acid sequence identity to the amino acid residues 16-35 of the 44-mer.

In other examples, it has been established that a 20-mer may prevent and/or ameliorating androgenic alopecia in a subject. Also, it is believed that the 20-mer is effective in treating alopecia and/or hair depigmentation caused by chemotherapy or stress, based on experiments disclosed in both the prior application and the present application. The 20-mer has the sequence of SLGAEQRTESIIHRALYYDL (SEQ ID NO: 6), which corresponds to residues 93-112 of human PEDF. This 20-mer peptide is completely identical to the amino acid residues 16-35 of the 44-mer (100% amino acid sequence identity), and has a 100% amino acid sequence identity to the 44-mer.

Two synthetic peptides derived from mouse PEDF may also prevent and/or ameliorating androgenic alopecia or alopecia and/or hair depigmentation induced by chemotherapy or stress in a subject based on experiments disclosed in both the prior application and the present application. The first mouse-derived peptide is referred to as "Mo 29-mer" in the present disclosure. The Mo 29-mer has a sequence of SLGAEHRTESVIHRALYYDLITNPDIHST (SEQ ID NO: 8), which has a 83% amino acid sequence identity to 44-mer, and the first 20 amino acid residues thereof has a 90% amino acid sequence identity to the 16-35 amino acid residues of the 44-mer. Another mouse-derived peptide, Mo 20-mer has a sequence of SLGAEHRTESVIHRALYYDL (SEQ ID NO: 9). The Mo 20-mer has a 90% amino acid sequence identity to both the 44-mer and the 16-35 amino acid residues of the 44-mer.

Optionally, the synthetic peptide comprises 4 consecutive residues identical to residues 16-19 of SEQ ID NO: 10. It is believed that residues 16-19 (i.e., SLGA) of SEQ ID NO: 10 play an important role in maintaining the biological function of the short PEDF peptides. For example, according to various examples provided below, an 18-mer peptide (EQRTESIIHRALYYDLIS; SEQ ID NO: 7) without the SLGA residues fails to elicit any protection for hair follicles in a subject. Also, based on experiments disclosed in both the prior application and the present application, it is suggested that a 25-mer peptide (EQRTESIIHRALYYDLISSPDIHGT; SEQ ID NO: 4) without the SLGA residues is not effective in treating alopecia and/or hair depigmentation in a subject.

The synthetic Peptides of the invention can be synthesized by commonly used methods such as t-BOC or FMOC protection of alpha-amino groups. Both methods involve stepwise syntheses whereby a single amino acid is added at each step starting from the C terminus of the peptide. Peptides of the present invention can also be synthesized by the well-known solid phase peptide synthesis methods.

Other synthetic peptides with conservative variation with respect to the 39-mer are also contemplated. The term "conservative variation" as used herein denotes the replacement of an amino acid residue by another, biologically similar residue. Examples of conservative variations include the substitution of one hydrophobic residue such as isoleucine, valine, leucine, or methionine for one another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

According to various embodiments of the present disclosure, the alopecia may be anagen effluvium (e.g., those caused by the chemotherapy or radiotherapy), telogen effluvium (e.g., those caused by the stress, diet imbalance, medications, or infections), or androgenic alopecia.

In some embodiments, the hair depigmentation may be caused by the chemotherapy or radiotherapy. In some other embodiments, the hair depigmentation may be caused by stress or aging.

According to various embodiments of the present disclosure, the subject may be any animal classified as a mammal, including human.

The synthetic peptides according to above-mentioned embodiments may be formulated into topical pharmaceutical compositions for treating alopecia and/or hair depigmentation in a subject, which falls within other aspects of the present disclosure.

According to one embodiment of the present disclosure, the topical pharmaceutical composition comprises a synthetic peptide according to any of the above-mentioned aspect/embodiments, and the synthetic peptide is present in an effective amount sufficient to treat alopecia and/or hair depigmentation in the subject. The pharmaceutical composition also comprises a pharmaceutically acceptable excipient for the synthetic peptide.

The pharmaceutical composition is prepared in accordance with acceptable pharmaceutical procedures, such as described in Remington's Pharmaceutical Sciences, $17^{th}$ edition, ed. Alfonoso R. Gennaro, Mack Publishing Company, Easton, Pa. (1985).

The choice of a pharmaceutically acceptable excipient to be used in conjunction with a synthetic peptide is basically determined by the way the topical pharmaceutical composition is to be administered. According to one optional embodiment of the present disclosure, the topical pharmaceutical composition may be spread, smeared, massaged, sprayed, or otherwise applied onto a biological surface (e.g., skin, scalp, or hair) of the subject such that the synthetic peptide may reach the target site (such as hair follicles) by the active absorption of hair follicles (the transappendageal route) or via transdermal delivery through transcellular pathway or intercellular pathway.

A wide variety of dermatologically acceptable inert excipients well known to the art may be employed. Typical inert excipients may be, for example, water, ethyl alcohol, polyvinyl pyrrolidone, propylene glycol, mineral oil, stearyl alcohol, ointment base, and gel-producing substances.

Optionally, pharmaceutical compositions of the invention can also comprise various pharmaceutically- (in particular, dermatologically-) acceptable additives well known to the art. Said additives include, but are not limited to, drying agent, anti-itch agents, anti-foaming agents, buffers, neutralizing agents, pH adjusting agents, coloring agents, discoloring agents, emollients, emulsifying agents, emulsion stabilizers, viscosity builders, humectants, odorants, preservatives, antioxidants, chemical stabilizers, thickening agents, stiffening agents, or suspending agents.

In various embodiments of the present disclosure, the topical pharmaceutical composition may be formulated in various dosage forms, such as a solution, spray, aerosol, foam, cream, lotion, ointment, gel, or patch.

According to optional embodiments of the present disclosure, the synthetic peptide is present in the pharmaceutical composition in an amount of about 0.1-100 µM, and preferably, about 1-25 µM. For example, the concentration of the synthetic peptides may be about 0.1, 0.2, 0.3, 0.4, 0.5, 0.3, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or 100 µM. Specifically, the concentration used in the working example below on mice (weighing about 20 grams) is about 25 µM. Persons having ordinary skills could calculate the human equivalent dose (HEQ) for the present synthetic peptide or pharmaceutical composition based on the animal doses provided herein. For example, the US Food and Drug Administration (FDA) has issued guidance for industry titled "Estimating the Maximum Safe Starting Dose in Initial Clinical Trials for Therapeutics in Adult Healthy Volunteers."

Optionally, the synthetic peptide may be formulated in a sustained-release dosage form so as to ensure a more prolonged therapeutic action of the treatment. For example, the synthetic peptide may be first encapsulated with a vehicle such as liposome, microsphere, or nanosome, and then formulated into a desired dosage form. Some of these vesicle-forming vehicles (e.g., liposome) are also advantageous in promoting the delivery rate of the present synthetic peptide or pharmaceutical composition.

Still optionally, the synthetic peptide may be formulated into a coating material which is later coated, impregnated, or otherwise retained on the surface or in the pores of a substrate thereby producing a patch or the like. The substrate may be prepared from at least one natural material, at least one synthetic material, or a combination of both. For example, the natural material may be collagen, hyaluronic acid, alginate, or chitosan, or derivatives thereof; while the synthetic material may be polyurethane, polyglycolic acid, or polyvinyl pyrrolidone, or derivatives thereof. Said coating material and/or substrate may have adequate bioadhesiveness such that the patch may be attached to the biological surface (e.g., scalp) of the subject and would not pose adverse effect on hair growth when the patch is removed.

In yet another aspect, the present invention is directed to a method for treating alopecia and/or hair depigmentation in a subject. The subject may be any animal classified as a mammal, including human.

In one embodiment, the method comprises administering to the subject an effective amount of the synthetic peptide according to any of the above-mentioned aspect/embodiments. According to various embodiment of the present disclosure, the synthetic peptide may be delivered topically or systemically. Preferably, the synthetic peptide is administered topically. More preferably, the synthetic peptide is topically administered onto a biological surface (e.g., skin, scalp, or hair) of the subject such that the synthetic peptide reaches the target site (e.g., hair follicles) so as to promote hair growth and/or hair pigmentation.

According to optional embodiments, the synthetic peptide is formulated into a topical pharmaceutical composition according to the above-mentioned aspect/embodiments of the present disclosure. In one example, the present topical pharmaceutical composition may be applied onto a biological surface (e.g., skin, scalp, or hair) of the subject.

Additionally, the synthetic peptide or the topical pharmaceutical compositions according to embodiments of the present disclosure may be administered under specified conditions (e.g., a specific humidity or temperature). For example, the administration under a more humid and warm environment may facilitate the adsorption of the synthetic peptide by the target site.

According to some embodiments, the subject may suffer from alopecia such as anagen effluvium, telogen effluvium, or androgenic alopecia, which causes abnormal hair loss. According to some other embodiment, the subject may suffer from hair depigmentation caused by chemotherapy, radiotherapy, oxidative stress, or aging. Also, the subject may suffer from alopecia and/or hair depigmentation due to his/hers genetic makeup.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

Materials

Dulbecco's modified Eagle's medium (DMEM), fetal bovine serum (FBS), and 0.25% trypsin were purchased from Invitrogen (Carlsbad, Calif.). Dihydrotestosterone (DHT), ethyl alcohol, 1-oleoyl-rac-glycerol, light mineral oil, hydroxypropyl methylcellulose, dimethyl sulfoxide (DMSO), insulin, hydrocortisone, bovine serum albumin (BSA), 5-bromo-2'-deoxyuridine (BrdU), Hoechst 33258 dye, and Hoechst 33342 dye were all from Sigma-Aldrich (St. Louis, Mo.). Anti-BrdU antibody was from GeneTex (Taipei, Taiwan). Anti-c-kit antibody (No. 3074) was from Cell Signaling Technology (No. 3074; Beverley, Mass., USA). Anti-tyrosinase antibody (No. sc-7833) and all the fluorescent dye-conjugated secondary antibodies were purchased from Santa Cruz Biotechnology (Santa Cruz, Calif.). Hematoxylin and eosin (H&E) dyes were purchased from Merck (Rayway, N.J., USA).

FITC-conjugated 29-mer and other short synthetic PEDF peptides, including 44-mer (SEQ ID NO: 10), 29-mer (SEQ ID NO: 3), 24-mer (SEQ ID NO: 5), 20-mer (SEQ ID NO: 6), 18-mer (SEQ ID NO: 7), and Mo 20-mer (SEQ ID NO: 9) were synthesized and modified by acetylation at the $NH_2$ termini and amidation at the COOH termini. The modified peptide were subsequently characterized by mass spectrometry (>95% purity) (GenScript (Piscataway, N.J.)).

Animals

All animals used in embodiments of the present disclosure were housed in an animal room under temperature control (24-25° C.) and 12:12 light-dark cycle. Standard laboratory chow and tap water were available ad libitum. The experiments procedures were approved by the Mackay Memorial Hospital Review Board (New Taipei City, Taiwan, R.O.C.) and were performed in compliance with national animal welfare regulations.

Topical Ointment or Gel Formulation

Each PEDF-derived short synthetic peptide (the FITC-conjugated 29-mer, 44-mer, 29-mer, 24-mer, 20-mer, 18-mer, or Mo 20-mer; hereinbelow, PEDF peptide) was reconstituted in DMSO as stock (5 mM) and stored at −20° C. for further use.

Before use, the stock containing the 44-mer was prepared into a working dilution, which is then mixed with an antibiotic ointment containing 5 mg/g neomycin sulfate and 12.5 mg/g bacitracin to obtain an antibiotic ointment containing 25 µM of 44-mer. As to other PEDF peptides, 5 µl of 5 mM PEDF peptide stock was gradually dissolved in ethyl alcohol (30% w/w in distilled water), and then 1-oleoyl-rac-glycerol (1% w/w, a skin penetration enhancer) and light mineral oil (1% w/w) were gradually added. The solution was finally gelled by adding hydroxypropyl methylcellulose (5% w/w) to a final volume of 1 ml. A DMSO vehicle corresponding to the peptide formulation was prepared for the purpose of in vivo comparison. FITC-29-mer was also dissolved in the same formulation for applied on top of skin to determining the follicular distribution of FITC-29-mer.

For topical treatments, 350 mg ointment or gel containing 25 µM of PEDF peptide was spread gently over dorsal skin per mouse.

Histology, Immunohistochemistry and Quantification

The murine back skin was harvested parallel to the vertebral line to obtain longitudinal sections through the hair follicles. Dorsal skin was fixed in 4% paraformaldehyde and embedded in paraffin blocks to obtain longitudinal section. Tissues were sliced into 5 µm sections. Before use, fixed samples were de-paraffinized in xylene and rehydrated in a graded series of ethanol. General histology was performed using H&E dye. Digital photomicrographs (Zeiss epifluorescence microscope; Jena, Germany) were taken from representative areas at a fixed magnification of 100×.

For analysis of HF morphogenesis, animals were euthanized at day 15 post-depilation. The percentage of hair follicles in different stages of morphogenesis was assessed on the accepted basis of murine HF morphological criteria as described by Müuller-Röver et al. (Journal of Investigative Dermatology (2001) 117, 3-15). At least 24 longitudinally cut HF sections obtained from six to ten DHT-treated animals, were analyzed. To demonstrate the PEDF peptide-dependent catagen retardation in DHT-treated skin, five-to-seven consecutive microscopic fields of a single representative skin section were taken and merged using a computer-assisted image analyzer (Adobe Photoshop CS3 10.0).

For immunostaining, de-paraffinized tissue sections were blocked with 10% goat serum for 1 hour. Dual staining was done using primary antibodies against c-kit (1:100 dilution; red) and tyrosinase (1:100 dilution) at 37° C. for 2 hours, followed by incubation with the rhodamine-conjugated goat anti-rabbit IgG antibody (1:500 dilution) for 1 hour at room temperature a before counterstaining with hematoxylin (blue) for about 7 minutes.

The vibrissae follicle cryosections were washed three times in PBS. Formalin-fixed, paraffin-embedded skin specimens were deparaffinized in xylene and rehydrated in a graded series of ethanol. Sections were then stained with TdT-mediated dUTP nick-end labeling (TUNEL)-based kit (Roche Molecular Biochemicals, Indianapolis, Ind.) following the manufacturer's instructions. The cell number was monitored by counterstaining with Hoechst 33258 (blue). The nuclei were calculated in ten randomly selected fields of the three different chambers by a Zeiss epifluorescence microscope (400×, 10 fields/sample). Pictures were recorded on Zeiss software.

After fixing with 4% paraformaldehyde, cells were exposed to cold methanol for 2 minutes, and then treated with 1 N HCl at room temperature for 1 hour before performing immunofluorescence. BrdU-labeled DNA was detected by polyclonal anti-BrdU antibody and rhodamine-conjugated donkey anti-rabbit IgG.

For animal study, BrdU was reconstituted in DMSO as stock (80 mM). 10 µl of BrdU mixed with 90 µl of PBS was intraperitoneally injected into mouse at 16 hours prior to euthanasia. Formalin-fixed, paraffin-embedded skin specimens were deparaffinized in xylene and rehydrated in a graded series of ethanol before performing immunohistochemistry. The vibrissae follicle cryosections were washed three times in PBS and then exposed to 1 N HCl at room temperature for 1 hour for subsequent immunohistochemistry.

Cell Culture

Mouse vibrissae follicles were cultured as follows. Briefly, whisker pads were cut off from the face of mouse and transferred to a Petri dish containing PBS and 1% antibiotic mixture. Each vibrissae follicle that was in anagen was isolated from the whisker pads and cultured in DMEM supplemented with insulin (10 µg/ml), hydrocortisone (10 ng/ml, Sigma-Aldrich), 1% penicillin/streptomycin antibiotic mixture and L-glutamine (2 mM), using 24-well culture plates (3 vibrissae follicles per well) and incubated at 37° C., in 5% $CO_2$. Ten to fifteen HFs were studied in each experimental group, and were repeated three times. DHT and PEDF peptide dissolved in DMSO were added to the HF culture supplemented with insulin and hydrocortisone (the final concentration of DMSO was less than 0.05%).

An immortalized human keratinocyte cell line (HaCaT) was cultured at 37° C. in 10% FBS-DMEM. Treatments with PEDF peptide and recombinant human TGFβ1 (R&D Systems) were performed on cells seeded in 5% FBS-DMEM.

Statistics

Results were expressed as the mean±standard error of the mean (SEM). One-way ANOVA was used for statistical comparisons. $P<0.05$ was considered significant, unless otherwise specified.

Example 1

PEDF Peptides Prevent/Ameliorate Hair Loss and Depigmentation Induced by Chemotherapy 6-week-old female C57BL/6 mice that had normal black fur (i.e., those had heavily melanized terminal hair shafts) were used in this example. In four independent experiments, a total of 80 mice were used. C57BL-6 mice have been widely used in the research of alopecia and hair-depigmentation induced by chemotherapy. Only mice in the resting stage of the hair cycle (telogen) were used in these studies. Since pigment production (melanogenesis) in mice occurs exclusively in anagen follicles, telogen C57BL-6 mice could be recognized by the homogeneously pink color of their back skin. Anagen was induced in the back skin of telogen mice by depilation.

In order to obtain mice that were in exactly the same stage of anagen development, the dorsal hairs were carefully shaved with an electric clipper. Nine days after the depilation, hair grown to anagen phase as judged by skin color from pink (telogen skin) to gray (early stage of anagen VI).

On day-9 post-depilation, mice were anesthetized by an intraperitoneal injection of a mixture of zoletil (6 mg/kg) and xylazine (3 mg/kg). Mice were randomly assigned to the following experimental groups. In the CYP/vehicle group, mice received intraperitoneal injection of cyclophosphamide (CYP, an anti-cancer drug) (150 mg/kg), and 350 mg antibiotic ointment was applied to the back skin at the same time. In the CYP/44-mer group, mice received intraperitoneal injection of CYP (150 mg/kg), and 350 mg antibiotic ointment containing 44-mer PEDF was applied to the back skin at the same time. In the vehicle group and 44-mer groups, mice were not intraperitoneally injected with CYP, and were treated with 350 mg antibiotic ointment and 350 mg antibiotic ointment containing 44-mer PEDF, respectively. After that, 350 mg antibiotic ointment (with or without 44-mer PEDF) was applied daily to the back skin of the mice for 7 days. For blank control, the mice were not treated with CYP injection nor the antibiotic ointment application.

Figure 1:
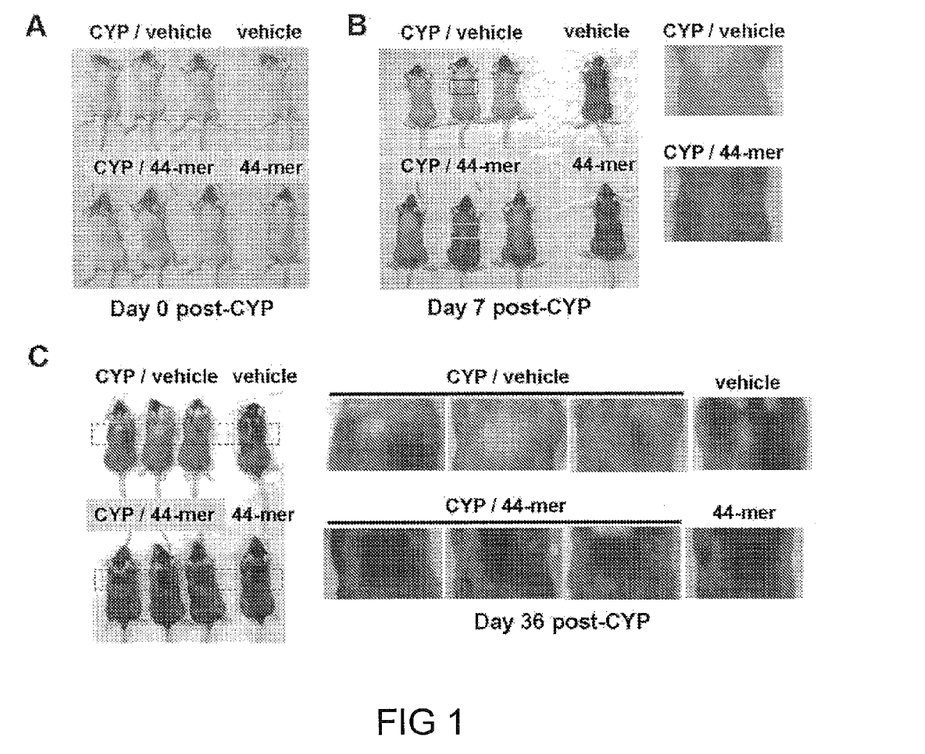
FIG. 1 provides representative photographs illustrating the appearance of hair-depilated mice in each experimental condition at 0, 7, and 36 days after CYP injection; high-powered macroscopic images corresponding to the marked rectangles are also provided FIG. 2 provides representative immunostained images illustrating TUNEL-positive apoptotic cells (green); nuclei were counterstained by Hoechst 33258 (blue); original magnification, ×1000.

FIG. 1 provides photographs of mice in each group on day-9 post-depilation (i.e., day-0 post-CYP injection), day-16 post-depilation (i.e., day-7 post-CYP injection), and day-45 post-depilation (i.e., day-36 post-CYP injection), respectively. By comparing the mice in CYP/vehicle and CYP/44-mer groups, we noted that CYP/44-mer mice respectively exhibited better hair growth activity on 7 and 36 days after the CYP injection.

Figure 2:
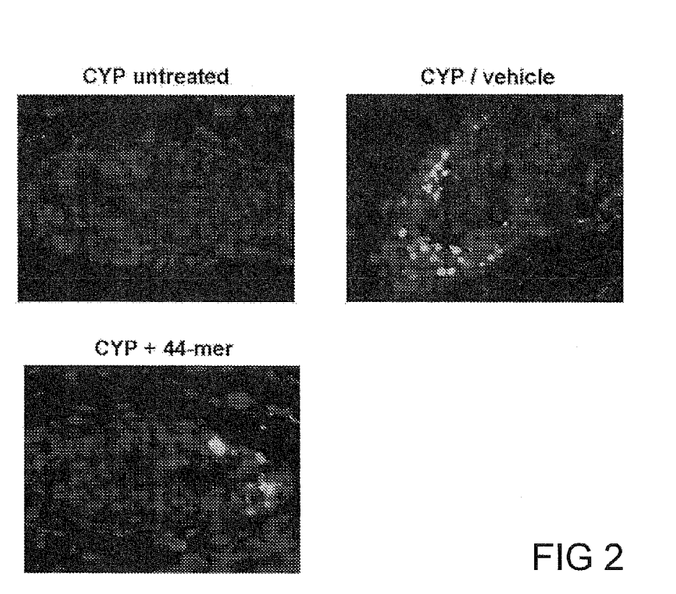

It is known that administering 150 mg/kg CYP to mice would cause apoptosis of keratinocytes as well as follicle dystrophy. Therefore, TUNEL staining was performed to stain the apoptotic cells to evaluate the protection effect of the PEDF peptides to the keratinocytes. FIG. 2 provide representative fluorescent images and quantitative results are summarized in Table 1. The labeling index (%) of TUNEL-positive cells was computed as the number of labeled cells divided by the total number of cells with nuclei.

TABLE 1

| Treatment | TUNNEL Labeling Index (%) |
| --- | --- |
| CYP/vehicle | 19.3 ± 1.7 |
| CYP/44-mer | 10.6 ± 1.4* |
| Vehicle | <0.1 |
| 44-mer | <0.1 |

*$P < 0.0005$ versus the CYP/vehicle group.

These results revealed that the numbers of apoptotic, TUNNEL-positive cells in mice treated with the 44-mer-containing ointment were significantly reduced, as compared with mice treated with the vehicle ointment only. Therefore, it is believed that the administration of the PEDF peptides may protect keratinocytes against the damage caused by chemotherapy agents (such as CYP), and thereby prevent and/or ameliorate hair loss caused by chemotherapy.

Melanocyte stem cells are responsible for supplying differentiated progenies such as melanoblasts and melanocytes to the hair root, and regulating the differentiation cycle of their progenies. Recent study indicates that abnormal differentiation of MSCs into mature melanocytes in the niche leads to the loss of MSCs and irreversible hair graying; this phenomenon is termed as "ectopically pigmented melanocytes (EPMs)."

Only the melanin residing in the hair bulb is capable of pigmenting the hair shaft. Specifically, the melanin granules produced by melanin in the hair bulb would be transported to the keratinocyte, thereby producing pigmented hairs. Moreover, a fully differentiated melanocyte undergoes apoptosis during the catagen phase and would be eliminated from the hair follicle. When the hair follicle experiences dystrophic anagen, the melanin level in the anagen follicle would reduce aberrantly and the melanin distribution is uneven, which results in melanin clump. For hairs experiencing dystrophic catagen, melanin would aggregate outside the hair bulb.

Still referring to FIG. 1, it is noted that 36 days after CYP injection, the mice in the CYP and CYP/vehicle groups had more gray and white hairs, while the mice in the CYP/44-mer group had substantially darker hairs. The results suggest that in CYP and CYP/vehicles groups, MSCs may be damaged by CYP, and therefore, they could not supply sufficient melanocytes for the production of melanin.

Figure 3:
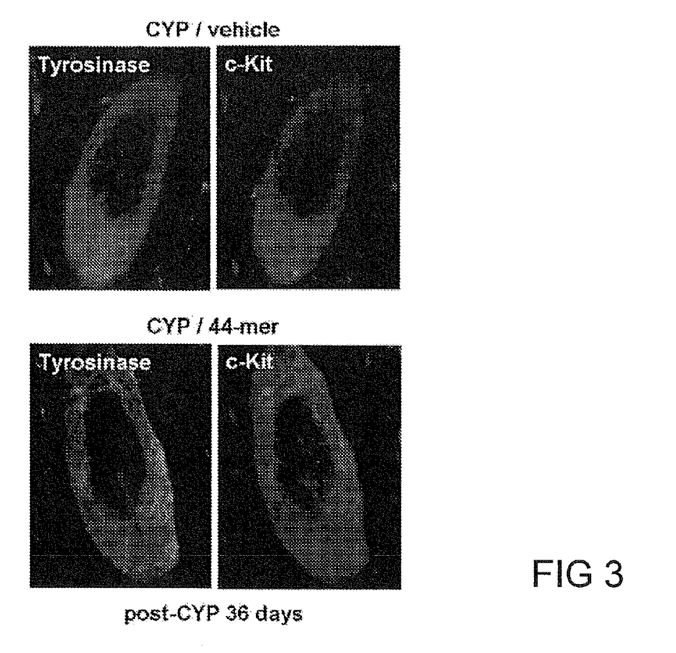
FIG. 3 provides representative photographs from hair follicle specimens assayed by dual-immunofluorescence staining for tyrosinase (green) and c-Kit (red); nuclei were stained by Hoechst 33258 (blue); original magnification, ×1000.

The activity of MSCs was evaluated by the expression of melanocyte lineage marker (c-kit) and tyrosinase. Referring to FIG. 3, the immunostaining analysis revealed that c-kit and tyrosinase expression were barely detected in the bulge of mice in the CYP/vehicle group, indicating that the MSC activity in the bulge is relatively low. By contrast, c-kit and tyrosinase expression were found in the bulge of mice in the CYP/44-mer group. Taken together, these data suggest that the present PEDF peptide is effective in protecting MSCs against the damage caused by CYP.

In conclusion, the results in Example 1 demonstrated that the 44-mer PEDF peptide is effective in reducing miniaturization of hair follicles, melanin clumping, and apoptosis of hair follicle cells and keratinocytes caused by CYP. Therefore, the 44-mer PEDF peptide is capable of preventing and/or ameliorating hair loss and/or hair depigmentation induced by chemotherapy. Moreover, our prior research and examples provided in Example 3 below indicated that physiological activities of a 39-mer PEDF derived from the 44-mer and several short PEDF peptide derived therefrom the 39-mer PEDF are similar to that of the 44-mer. Hence, we inferred that these short, synthetic PEDF peptides, including SEQ ID NO: 1 (39-mer), SEQ ID NO: 2 (34-mer), SEQ ID NO: 3 (29-mer), SEQ ID NO: 5 (24-mer), SEQ ID NO: 6 (20-mer), SEQ ID NO: 8 (MO 29-mer), and SEQ ID NO: 9 (MO 20-mer), are also effective in treating alopecia and/or hair depigmentation induced by chemotherapy.

Example 2

PEDF Peptides Prevent/Ameliorate Hair Loss and Depigmentation Induced by Stress

Various environmental and endogenous factors, such as ultraviolet radiation, inflammation, or psychoemotion, are known to cause oxidative stress, which in terms accelerates the aging process. Also, the subject's genetic makeup may also affect his/hers tolerance to these factors. Prior study established that there are several micromoles of hydrogen peroxide within the aged hair follicles. Also, it has been confirmed in animal models that the endogenous oxidative stress would increase the apoptosis of melanocytes in the hair follicles, which eventually leads to hair graying.

In this example, the relationships between the stress caused by endogenous challenge (e.g., oxidants) and hair loss and hair graying were investigated. The mice were selected and depilated as described in Example 1 above. On day-9 post-depilation, the mice were subcutaneously injected with hydrogen peroxide at a dose of 10 ml/kg body weight. As comparison, 350 mg antibiotic ointment with or without 44-mer PEDF were respectively applied to the back skins of mice in H2O2/vehicle and H2O2/44-mer groups.

Figure 4:
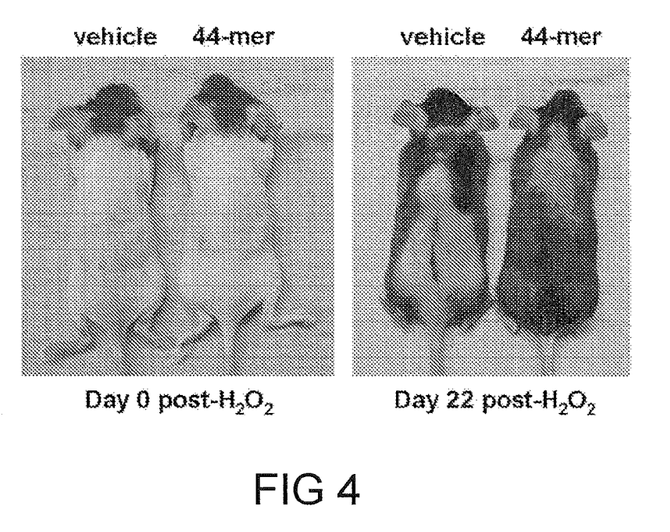
FIG. 4 provides representative photographs illustrating the appearance of mice in each experimental condition at 0 and 22 days after hydrogen peroxide subcutaneously injection.

FIG. 4 provides photographs of the mice in each group on day-9 post-depilation (i.e., day-0 post-$H_2O_2$ injection) and day-31 post-depilation (i.e., day-22 post-$H_2O_2$ injection), respectively. By comparing the mice in $H_2O_2$/vehicle and $H_2O_2$/44-mer groups, it is noted that $H_2O_2$/44-mer mice exhibited better hair growth activity 22 days after the $H_2O_2$ injection. Also, the hair color was darker in mice treated with the antibiotic ointment containing 25 µM of 44-mer PEDF. Therefore, the 44-mer PEDF is effective in preventing and/or ameliorating hair loss and/or hair depigmentation caused by stress (such as the oxidative stress).

Further, as our prior research and Example 3 below indicated, physiological activities of several short PEDF peptides derived from the 44-mer PEDF are similar to that of the 44-mer. Hence, the results suggest that these short, synthetic PEDF peptides, including SEQ ID NO: 1 (39-mer), SEQ ID NO: 2 (34-mer), SEQ ID NO: 3 (29-mer), SEQ ID NO: 5 (24-mer), SEQ ID NO: 6 (20-mer), SEQ ID NO: 8 (MO 29-mer), and SEQ ID NO: 9 (MO 20-mer), are also effective in treating alopecia and/or hair depigmentation induced by stress.

Example 3

PEDF Peptides Prevent/Ameliorate Androgenic Alopecia

In vitro and in vivo analyses were carried out to evaluate the effect of the present PEDF peptides on androgenic alopecia.

Example 3.1

Figure 5:
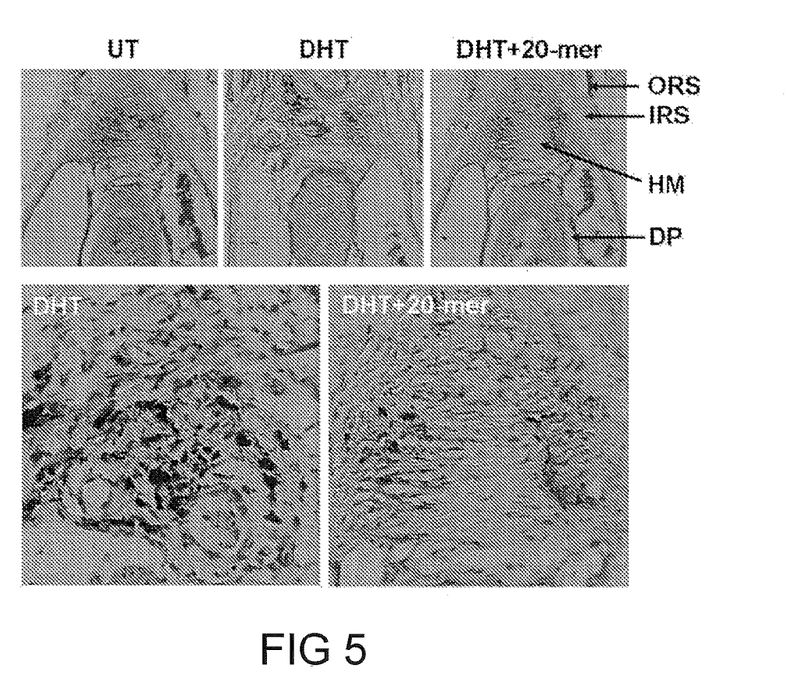
FIG. 5 provides representative photographs from the mid-anagen hair follicles of mouse vibrissa specimens stained by hematoxylin and eosin (H&E); ORS, outer root sheath; IRS, inner root sheath; DP, dermal papilla; HM, hair matrix; original magnification in upper panel, ×100; original magnification in lower panel, ×400.

PEDF Peptides Antagonize Growth Arrest and Apoptosis of Keratinocytes Induced by DHT In Vitro Each PEDF peptide (29-mer, 24-mer, 20-mer, or Mo 20-mer) was added to organ culture of male mouse vibrissal hair follicles (HFs) for 16 hours, and then 100 nM DHT was added for further 48 hours. Histologic analysis at higher magnification revealed that DHT caused hair matrix with cellular disorganization and melanin clumps, as compared with untreated HFs (FIG. 5). By contrast, most region of the hair matrix in 20-mer PEDF-pretreated HFs had regularly aligned keratinocytes and much less abnormal melanin particles (FIG. 5).

Immunodetections of TUNEL- and BrdU-positive cells in cryosections were used for assessing apoptosis and proliferation activity in the HF epithelium, respectively. Quantitative results are summarized in Table 2. The labeling index (%) of TUNEL- and BrdU-positive cells was computed as the number of labeled cells divided by the total number of cells with nuclei.

TABLE 2

| Treatment | TUNNEL Labeling Index (%) | BrdU Labeling Index (%) |
|---|---|---|
| Untreated | 1.7 ± 0.76 | 15.8 ± 2.08 |
| DHT/vehicle | 28.5 ± 4.90* | 9.0 ± 1.92# |

TABLE 2-continued

| Treatment | TUNNEL Labeling Index (%) | BrdU Labeling Index (%) |
|---|---|---|
| DHT/29-mer | 5.8 ± 2.12** | 22.6 ± 2.42## |
| DHT/24-mer | 6.5 ± 2.43** | 22.0 ± 3.69## |
| DHT/20-mer | 6.8 ± 1.68** | 23.6 ± 4.56## |
| DHT/Mo 20-mer | 7.3 ± 1.75** | 24.6 ± 2.56## |
| DHT/18-mer | 26.2 ± 4.21 | 8.4 ± 1.21 |

*$P < 0.00001$ versus the untreated group;
**$P < 0.00007$ versus the DHT/vehicle group.
$P < 0.05$ versus the untreated group;
$P < 0.002$ versus the DHT/vehicle group.

As could be seen in Table 2, the in vitro spontaneous keratinocyte apoptosis in hair matrix was very low (1.7±0.76%; the untreated group), whereas significant cell death was observed in keratinocytes surrounding dermal papilla (DP) in the presence of 100 nM DHT (28.5±4.90%; the DHT/vehicle group). Also, vibrissae treated with PEDF peptides of the present disclosure (e.g., 29-mer, 24-mer, 20-mer, and Mo 20-mer) exhibited much less TUNEL-positive keratinocytes, as compared with vibrissae treated with vehicle or the 18-mer PEDF peptide. These results suggested that the present PEDF treatments are effective in reducing keratinocyte apoptosis induced by DHT.

The results in Table 2 also showed that the cell division of keratinocytes in hair matrix was suppressed by DHT, as compared with untreated HFs (DHT/vehicle: 9.0±1.92% versus Untreated: 15.8±2.08%). On the other hand, higher BrdU labeling index for cells treated with the present PEDF peptides indicated an improvement in the proliferative activity of follicular keratinocytes by the present treatment.

It is known that DHT would induce the expression of transforming growth factor-β1 (TGF-β1) in dermal papilla cells (DPCs), and TGF-β1 is a catagen inducer that suppresses hair growth and follicular keratinocyte growth in subjects with androgenic alopecia. To further confirm that PEDF-derived peptide is able to protect keratinocytes from DHT-mediated growth suppression, the cell division of human epidermal keratinocytes (HaCaT) in response to TGF-β1 and PEDF-derived peptide were assessed by BrdU incorporation. Quantitative results are summarized in Table 3. The labeling index (%) of BrdU-positive cells was computed as the number of labeled cells divided by the total number of cells with nuclei.

TABLE 3

| Treatment | BrdU Labeling Index (%) |
|---|---|
| Untreated | 23.6 ± 2.84 |
| TGF-β1 | 9.9 ± 2.23* |
| 20-mer | 23.3 ± 2.46 |
| TGF-β1 + 20-mer | 32.3 ± 3.70** |

*$P < 0.002$ versus untreated cells;
**$P < 0.0001$ versus TGF-β1 treated cells.

As could be seen in Table 3, treatment of HaCaT with TGF-β1 (4 ng/ml, 24 hours) substantially reduced the levels of BrdU-positive cells, as compared with that of untreated cells. However, in the TGF-β1+20-mer treatment group, TGF-β1 was unable to suppress the proliferative activity of HaCaT, when cells were pretreated with 20-mer for 16 hours.

Taken together, PEDF-derived peptides may block the anti-proliferative effect of DHT (and TGFβ1) on keratinocytes.

Example 3.2

PEDF Peptides Retards Catagen Development Induced by DHT In Vivo

For in vivo analysis, a 5α-dihydrotestosterone (DHT) animal model was employed. Six-week-old male C57BL/6 mice (weighing 15-20 g) in the telogen stage of the hair cycle were depilated using a melted wax/rosin mixture (1:1) under general anesthesia, and the anagen stage was induced. DHT was dissolved in DMSO to give a 50 mg/ml stock solution. On day-11 post-depilation, mice (six to ten mice per experimental condition) were injected subcutaneously in the shaved dorsal area with DHT solution (30 mg/kg body weight; 1.5 mg of DHT mixed within 200 μl of olive oil per mouse). After the DHT injection, 350 mg vehicle gel or gel containing 25 μM of PEDF peptide (29-mer, 24-mer, 20-mer, or 18-mer) was topically applied to the back skin of mice once per day for 3 days.

Figure 6:
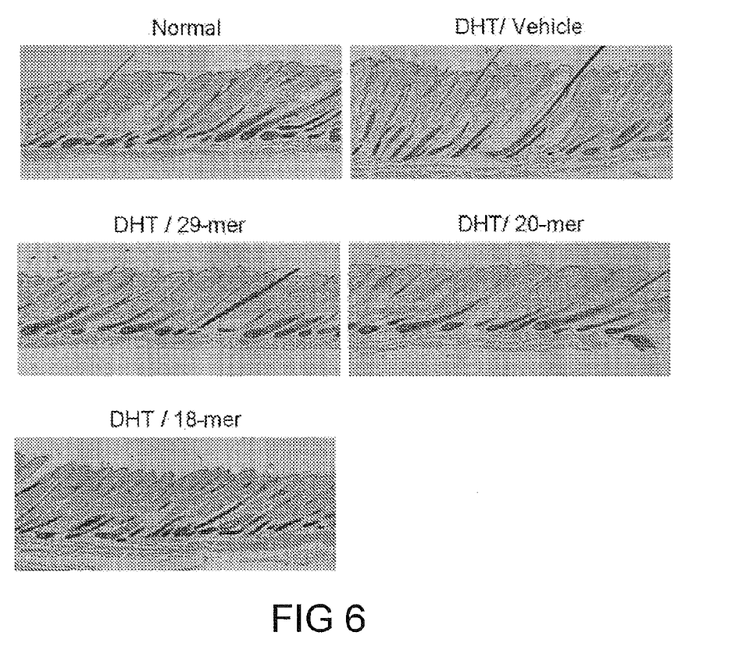
FIG. 6 provides representative photographs from the dorsal skin of mouse stained by H&E; original magnification, ×100.

As presented in FIG. 6, histological analysis performed on day-15 post-depilation (i.e., 4 days after the DHT injection) revealed that HFs from mice that were not treated DHT (Untreated group) is composed of anagen and spontaneous onset of catagen, whereas HFs of DHT/vehicle and DHT/18-mer mice entered catagen as expected. By contrast, HFs of mice treated with 29-mer and 20-mer were mostly in the anagen phase, indicating that catagen progression enhanced by DHT was blocked. The quantitative assessment regarding the percentage of hair follicles in each cycle phase in each experimental group was summarized in Table 4.

TABLE 4

| Treatment | Phase (%) | | | |
| --- | --- | --- | --- | --- |
| | Anagen-Catagen I | Catagen II-III | Catagen IV-V | Catagen VI-VIII |
| Untreated | 58.3 ± 1.7 | 28.85 ± 2.95 | 17.35 ± 1.25 | 0 ± 0 |
| DHT/vehicle | 7.85 ± 2.75* | 13.0 ± 4.0 | 54.65 ± 3.05 | 34.5 ± 3.7 |
| DHT/29-mer | 39.85 ± 1.35** | 37.8 ± 1.3 | 19.15 ± 2.05 | 3.2 ± 0.6# |
| DHT/20-mer | 39.0 ± 2.8** | 33.95 ± 1.25 | 23.6 ± 1.8 | 3.45 ± 0.25# |
| DHT/18-mer | 9.7 ± 1.8 | 13.85 ± 1.75 | 53.05 ± 0.85 | 23.4 ± 4.4 |

*$P < 0.001$ versus the untreated group;
**$P < 0.02$ versus the DHT/vehicle group.
$P < 0.005$ versus the DHT/vehicle group.

The data in Table 4 indicated that in the DHT/29-mer, DHT/24-mer, and DHT/20-mer groups, a significantly higher percentage of hair follicles was found in the anagen phase, and the early catagen phase (catagen phase I to III). On the other hand, a majority of hair follicles in mice treated with vehicle or 18-mer, was in the middle and late catagen phase (catagen phase IV to VIII).

To confirm the above histomorphometric analysis, BrdU and TUNEL staining were performed on day-15 post-depilation. Quantitative results were summarized in Table 5. Numbers of TUNNEL-positive cells in the hair matrix (HM) and outer root sheath (ORS) were expressed as TUNEL-positive cells per hair follicle. The labeling index (%) of BrdU-positive cells in the hair bulb (HB) was computed as the number of labeled cells divided by the total number of cells with nuclei.

TABLE 5

| Treatment | TUNNEL-positive cell/HF in HM and ORS | BrdU Labeling Index (%) in HB |
| --- | --- | --- |
| Untreated | 0.30 ± 0.15 | 43.4 ± 3.38 |
| DHT/vehicle | 7.5 ± 1.5* | 26.4 ± 2.92# |
| DHT/29-mer | 0.57 ± 0.34** | 44.89 ± 2.95## |
| DHT/24-mer | 0.73 ± 0.46** | 46.9 ± 2.57## |
| DHT/20-mer | 0.71 ± 0.30** | 45.2 ± 2.47## |
| DHT/18-mer | 7.6 ± 1.5 | 25.6 ± 2.52 |

*$P < 0.0002$ versus the untreated group;
**$P < 0.007$ versus the DHT/vehicle group.
$P < 0.002$ versus the untreated group;
$P < 0.004$ versus the DHT/vehicle group.

By comparing the untreated and DHT/vehicle groups, it is observed that DHT injection enhanced catagen development, as demonstrated by a dramatically increased amount of TUNEL-positive cells in the hair matrix and outer root sheath (ORS) along with a decrease in the proliferation activity in the proximal anagen HF. In DHT-injected mice treated with 20-mer, 24-mer, or 29-mer, the mice had almost no TUNEL-positive cells (less than 1) per HF and dense clusters of BrdU-positive keratinocytes, confirming that the present PEDF peptides antagonize DHT effect on hair follicle regression.

Collectively, DHT-induced catagen transition as evident from cell proliferation arrest and apoptosis of follicular keratinocytes is blocked by topical application with the present PEDF-derived peptides (e.g., 29-mer, 24-mer and 20-mer). These results confirm that the present PEDF-derived peptides may retard DHT-induced premature anagen to catagen transition.

Example 3.3

PEDF Peptides Sustain Developing Hair Follicles In Vivo

To evaluate the effect of PEDF peptide on restarting hair growth, C57BL/6 mice were depilated as described in Example 3.2. At day-11 post-depilation, mice (six to ten mice per experimental condition) were injected subcutaneously (30 mg/kg body weight) in the shaved dorsal area with DHT solution (1.5 mg of DHT mixed within 200 μl of olive oil), and then the mice were injected with DHT twice per week during the course of the study. After the first DHT injection, 350 mg vehicle gel or gel containing 25 μM PEDF peptide (29-mer, 24-mer, 20-mer, or 18-mer) was topically applied to the back skin of mice once per day for 14 days. Changes in hair coat were recorded by photographing with a digital camera (FIG. 7), and the percentage of the shaved area that became dark (re-grown hair) was measured. The scores of hair regrowth after DHT injection was evaluated using the following scale: 0, 0% (no hair growth); 1, <20%; 2, 20-39%; 3, 40-59%; 4, 60-79%; 5, 80-100%. Numbers of hair bulbs per unit length (1 mm) of deep subcutis were counted as described above. Results were summarized in Table 6.

TABLE 6

| Treatment | Hair Growth Score | Numbers of Hair Bulbs/mm deep subcutis |
| --- | --- | --- |
| Untreated | 5 ± 0 | 8.8 ± 0.58 |
| DHT/vehicle | 1.75 ± 0.45* | 4.4 ± 0.51† |
| DHT/29-mer | 3.75 ± 0.37** | 7.4 ± 1.03†† |
| DHT/24-mer | 4.13 ± 0.40** | 7.2 ± 1.07†† |

TABLE 6-continued

| Treatment | Hair Growth Score | Numbers of Hair Bulbs/mm deep subcutis |
|---|---|---|
| DHT/20-mer | 4.25 ± 0.25** | 6.8 ± 1.24†† |
| DHT/18-mer | 1.88 ± 0.40 | 4.8 ± 0.86 |

*P < 0.0001 versus the untreated group;
**P < 0.02 versus the DHT/vehicle group.
†P < 0.0005 versus the untreated group;
††P < 0.002 versus the DHT/vehicle group.

Figure 7:
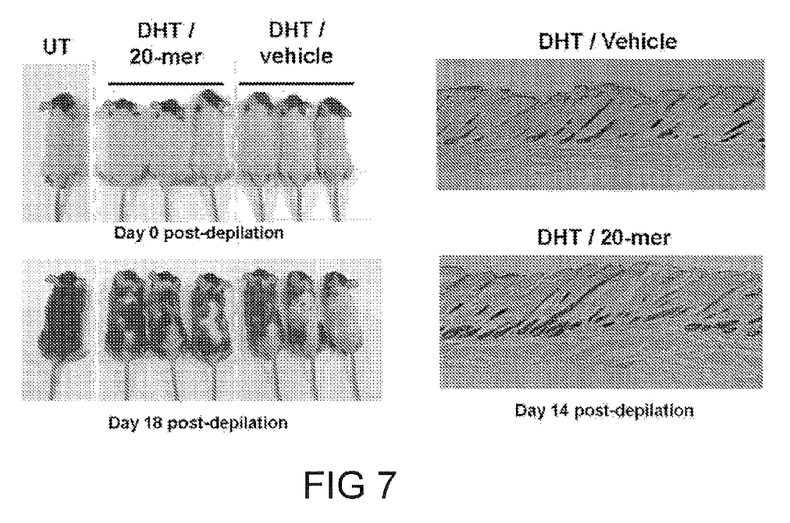
FIG. 7 provides representative photographs illustrating the hair regrowth in each experimental condition at 0 and 18 days after hair depilation, and representative photographs from dorsal skin specimens stained by hematoxylin and eosin (H&E); original magnification, ×100.

The results in FIG. 7 and Table 6 indicated that the growth phase of the hair cycle (anagen) was induced in the dorsal skin by depilation (untreated group). By contrast, mice in the DHT/vehicle and DHT/18-mer groups exhibited a remarkable retardation of hair regrowth ever at day-18 post-depilation; this is an expected finding of a well-accepted animal model of androgenic alopecia. On the other hand, DHT-injected mice treated with daily application of 29-mer, 24-mer, or 20-mer exhibited an amelioration of the retardation of hair regrowth and substantial hair growth occurred. Results of statistical analysis indicated that DHT-injected mice treated with 29-mer, 24-mer, and 20-mer displayed a better growth score after depilation than the DHT/vehicle control group.

Still referring to Table 6, a significantly increased total number (1.6-fold) of hair bulbs was found in mice treated with either 29-mer, 24-mer or 20-mer, as compared with mice treated with the vehicle or 18-mer. These results suggested that a significant number of HF escaped the effect of DHT and moved into the anagen phase under the protective effect of the present PEDF peptides.

In conclusion, data presented in Example 3 (including Examples 3.1 to 3.3) demonstrated that the present PEDF peptides were effective in treating hair loss induced by DHT. Hence, the topical administration of the PEDF peptides would prevent or ameliorate the hair loss caused by androgenic alopecia.

The present disclosure is the first to demonstrate that topical application of short, synthetic PEDF peptides has therapeutic effect on hair follicle. As compared with the conventional intravenous or intramuscular delivery of vectors expressing full-length PEDF peptides, topical delivery of short synthetic PEDF peptides is a safe and less expensive approach.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating alopecia or hair depigmentation in a subject, comprising administering to the subject in need thereof a composition comprising a therapeutically effective amount of synthetic peptide consisting of an amino acid sequence having 20-39 amino acid residues in length, wherein the amino acid sequence at least includes a sequence selected from the group consisting of SEQ ID NOs: 1-3, 5, 6, and 8-9.

2. The method according to claim 1, wherein 4 consecutive residues of the synthetic peptide are identical to residues 16-19 of SEQ ID NO: 10.

3. The method according to claim 1, wherein the alopecia is anagen effluvium or androgenic alopecia.

4. The method according to claim 1, wherein the hair depigmentation is caused by chemotherapy, radiotherapy, stress, genetic, or aging.

5. The method according to claim 1, wherein the subject is a human subject.

6. The method according to claim 1, wherein the composition is a topical pharmaceutical composition comprising, an effective amount of the synthetic peptide; and a pharmaceutically acceptable excipient.

7. The method according to claim 6, wherein 4 consecutive residues of the synthetic peptide are identical to residues 16-19 of SEQ ID NO: 10.

8. The method according to claim 6, wherein the topical pharmaceutical composition is in the form of a solution, spray, aerosol, foam, cream, lotion, ointment, gel, or patch.

9. The method according to claim 6, wherein the alopecia is anagen effluvium or androgenic alopecia.

10. The method according to claim 6, wherein the hair depigmentation is caused by chemotherapy, radiotherapy, stress, genetic, or aging.

11. The method according to claim 6, wherein the subject is a human subject.

12. The method according to claim 1, wherein the synthetic peptide has the amino acid sequence of SEQ ID NO:1, SEQ ID NO:2, SEQ ID NO:3, SEQ ID NO:5, SEQ ID NO:6, SEQ ID NO:8, or SEQ ID NO:9.

13. The method according to claim 1, wherein the synthetic peptide has the amino acid sequence of SEQ ID NO:3, SEQ ID NO:5, or SEQ ID NO:6.

14. The method of claim 12, wherein the synthetic peptide is formulated into a topical pharmaceutical composition comprising the synthetic peptide and a pharmaceutically acceptable excipient.

15. The method of claim 14, wherein the topical pharmaceutical composition is in the form of a solution, spray, aerosol, foam, cream, lotion, ointment, gel, or patch.

16. The method of claim 14, wherein the synthetic peptide is present in the pharmaceutical composition at a concentration of 0.1-100 µM.

17. The method of claim 16, wherein the concentration is 1-25 µM.

18. The method of claim 12, wherein the alopecia is anagen effluvium or androgenic alopecia.

19. The method of claim 12, wherein the hair depigmentation is caused by chemotherapy, radiotherapy, stress, genetic, or aging.

20. The method of claim 12, wherein the subject is a human subject.

21. The method according to claim 1, wherein the synthetic peptide consists of an amino acid sequence having 20-29 amino acid residues in length, and wherein the amino acid sequence at least includes a sequence selected from the group consisting of SEQ ID NOs: 3, 5, 6, and 8-9.

* * * * *

SEQUENCE LISTING

```
<160> NUMBER OF SEQ ID NOS: 11

<210> SEQ ID NO 1
<211> LENGTH: 39
<212> TYPE: PRT
<213> ORGANISM: Artificial Sequence
<220> FEATURE:
<223> OTHER INFORMATION: synthetic peptide

<400> SEQUENCE: 1

Leu Ser Val Ala Thr Ala Leu Ser Ala Leu Ser Leu Gly Ala Glu Gln
1               5                   10                  15

Arg Thr Glu Ser Ile Ile His Arg Ala Leu Tyr Tyr Asp Leu Ile Ser
            20                  25                  30

Ser Pro Asp Ile His Gly Thr
        35

<210> SEQ ID NO 2
<211> LENGTH: 34
<212> TYPE: PRT
<213> ORGANISM: Artificial Sequence
<220> FEATURE:
<223> OTHER INFORMATION: synthetic peptide

<400> SEQUENCE: 2

Ala Leu Ser Ala Leu Ser Leu Gly Ala Glu Gln Arg Thr Glu Ser Ile
1               5                   10                  15

Ile His Arg Ala Leu Tyr Tyr Asp Leu Ile Ser Ser Pro Asp Ile His
            20                  25                  30

Gly Thr

<210> SEQ ID NO 3
<211> LENGTH: 29
```

```
<212> TYPE: PRT
<213> ORGANISM: Artificial Sequence
<220> FEATURE:
<223> OTHER INFORMATION: synthetic peptide

<400> SEQUENCE: 3

Ser Leu Gly Ala Glu Gln Arg Thr Glu Ser Ile Ile His Arg Ala Leu
1               5                   10                  15

Tyr Tyr Asp Leu Ile Ser Ser Pro Asp Ile His Gly Thr
            20                  25

<210> SEQ ID NO 4
<211> LENGTH: 25
<212> TYPE: PRT
<213> ORGANISM: Artificial Sequence
<220> FEATURE:
<223> OTHER INFORMATION: synthetic peptide

<400> SEQUENCE: 4

Glu Gln Arg Thr Glu Ser Ile Ile His Arg Ala Leu Tyr Tyr Asp Leu
1               5                   10                  15

Ile Ser Ser Pro Asp Ile His Gly Thr
            20                  25

<210> SEQ ID NO 5
<211> LENGTH: 24
<212> TYPE: PRT
<213> ORGANISM: Artificial Sequence
<220> FEATURE:
<223> OTHER INFORMATION: synthetic peptide

<400> SEQUENCE: 5

Ser Leu Gly Ala Glu Gln Arg Thr Glu Ser Ile Ile His Arg Ala Leu
1               5                   10                  15

Tyr Tyr Asp Leu Ile Ser Ser Pro
            20

<210> SEQ ID NO 6
<211> LENGTH: 20
<212> TYPE: PRT
<213> ORGANISM: Artificial Sequence
<220> FEATURE:
<223> OTHER INFORMATION: synthetic peptide

<400> SEQUENCE: 6

Ser Leu Gly Ala Glu Gln Arg Thr Glu Ser Ile Ile His Arg Ala Leu
1               5                   10                  15

Tyr Tyr Asp Leu
            20

<210> SEQ ID NO 7
<211> LENGTH: 18
<212> TYPE: PRT
<213> ORGANISM: Artificial Sequence
<220> FEATURE:
<223> OTHER INFORMATION: synthetic peptide

<400> SEQUENCE: 7

Glu Gln Arg Thr Glu Ser Ile Ile His Arg Ala Leu Tyr Tyr Asp Leu
1               5                   10                  15

Ile Ser

<210> SEQ ID NO 8
<211> LENGTH: 29
```

```
<212> TYPE: PRT
<213> ORGANISM: Artificial Sequence
<220> FEATURE:
<223> OTHER INFORMATION: synthetic peptide

<400> SEQUENCE: 8

Ser Leu Gly Ala Glu His Arg Thr Glu Ser Val Ile His Arg Ala Leu
1               5                   10                  15

Tyr Tyr Asp Leu Ile Thr Asn Pro Asp Ile His Ser Thr
            20                  25

<210> SEQ ID NO 9
<211> LENGTH: 20
<212> TYPE: PRT
<213> ORGANISM: Artificial Sequence
<220> FEATURE:
<223> OTHER INFORMATION: synthetic peptide

<400> SEQUENCE: 9

Ser Leu Gly Ala Glu His Arg Thr Glu Ser Val Ile His Arg Ala Leu
1               5                   10                  15

Tyr Tyr Asp Leu
            20

<210> SEQ ID NO 10
<211> LENGTH: 44
<212> TYPE: PRT
<213> ORGANISM: Artificial Sequence
<220> FEATURE:
<223> OTHER INFORMATION: synthetic peptide

<400> SEQUENCE: 10

Val Leu Leu Ser Pro Leu Ser Val Ala Thr Ala Leu Ser Ala Leu Ser
1               5                   10                  15

Leu Gly Ala Glu Gln Arg Thr Glu Ser Ile Ile His Arg Ala Leu Tyr
            20                  25                  30

Tyr Asp Leu Ile Ser Ser Pro Asp Ile His Gly Thr
            35                  40

<210> SEQ ID NO 11
<211> LENGTH: 418
<212> TYPE: PRT
<213> ORGANISM: Homo sapiens

<400> SEQUENCE: 11

Met Gln Ala Leu Val Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Glu Asp Pro Phe Phe Lys
            35                  40                  45

Val Pro Val Asn Lys Leu Ala Ala Ala Val Ser Asn Phe Gly Tyr Asp
        50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
            115                 120                 125
```

-continued

```
Val Thr Ala Pro Gln Lys Asn Leu Lys Ser Ala Ser Arg Ile Val Phe
        130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
        210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
                260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
            290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
                340                 345                 350

Leu Thr Gln Val Glu His Arg Ala Gly Phe Glu Trp Asn Glu Asp Gly
                355                 360                 365

Ala Gly Thr Thr Pro Ser Pro Gly Leu Gln Pro Ala His Leu Thr Phe
        370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro
```